(12) United States Patent
Bilal et al.

(10) Patent No.: US 11,648,212 B2
(45) Date of Patent: *May 16, 2023

(54) LOXAPINE FILM ORAL DOSAGE FORM

(71) Applicant: Intelgenx Corp., St-Laurent (CA)

(72) Inventors: Mobarik Bilal, Montreal (CA);
Rodolphe Obeid, Pierrefonds (CA);
Nadine Paiement, St-Laurent (CA)

(73) Assignee: Intelgenx Corp., St-Laurent (CA)

( * ) Notice: Subject to any disclaimer, the term of this patent is extended or adjusted under 35 U.S.C. 154(b) by 617 days.

This patent is subject to a terminal disclaimer.

(21) Appl. No.: 16/053,383

(22) Filed: Aug. 2, 2018

(65) Prior Publication Data

US 2019/0000770 A1 Jan. 3, 2019

Related U.S. Application Data

(63) Continuation-in-part of application No. 15/014,269, filed on Feb. 3, 2016.

(51) Int. Cl.
*A61K 31/553* (2006.01)
*A61K 47/10* (2017.01)
(Continued)

(52) U.S. Cl.
CPC ............ *A61K 9/7015* (2013.01); *A61K 9/006* (2013.01); *A61K 9/7007* (2013.01);
(Continued)

(58) Field of Classification Search
CPC .... A61K 9/7015; A61K 47/26; A61K 47/186; A61K 9/7007; A61K 47/38;
(Continued)

(56) References Cited

U.S. PATENT DOCUMENTS

2003/0060487 A1   3/2003  Bamdad et al.
2005/0226823 A1*  10/2005  Krumme ................ A61K 9/006
                                                                424/53

(Continued)

OTHER PUBLICATIONS

Krise, Jeffrey P., et al., "A Novel Prodrug Approach for Tertiary Amines. 2, Physicochemical and In Vitro Enzymatic Evaluation of Selected N-Phosphonooxymethyl Prodrugs," Journal of Pharmaceutical Sciences, vol. 88, No. 9, Sep. 1999, pp. 922-927, (6 pages).

*Primary Examiner* — Savitha M Rao
*Assistant Examiner* — Andrew P Lee
(74) *Attorney, Agent, or Firm* — Gunther Evanina; Butzel Long

(57) ABSTRACT

A loxapine film oral dosage form includes loxapine salt, free base, or prodrug in an amount effective to provide relief from acute agitation associated with schizophrenia or bipolar 1 disorder via oral transmucosal delivery, dispersed in a polymeric film forming system. Advantageously, the film oral dosage form further includes a sweetener, a refreshing agent, an antioxidant, a pH stabilizer, a penetration enhancer, a mucoadhesive agent and a plasticizer. The loxapine film oral dosage form provides rapid onset of relief from acute agitation associated with schizophrenia or bipolar 1 disorder without presenting pulmonary health risks, thereby reducing risks to patients and others.

12 Claims, 3 Drawing Sheets

(51) Int. Cl.
   *A61K 47/28*   (2006.01)
   *A61K 9/70*    (2006.01)
   *A61K 9/00*    (2006.01)
   *A61K 47/36*   (2006.01)
   *A61K 47/32*   (2006.01)
   *A61K 47/26*   (2006.01)
   *A61K 47/18*   (2017.01)
   *A61K 47/38*   (2006.01)

(52) U.S. Cl.
   CPC ............ *A61K 31/553* (2013.01); *A61K 47/10* (2013.01); *A61K 47/186* (2013.01); *A61K 47/26* (2013.01); *A61K 47/28* (2013.01); *A61K 47/32* (2013.01); *A61K 47/36* (2013.01); *A61K 47/38* (2013.01)

(58) Field of Classification Search
   CPC ...... A61K 31/553; A61K 9/006; A61K 47/28; A61K 47/10; A61K 47/36; A61K 47/32
   See application file for complete search history.

(56) References Cited

U.S. PATENT DOCUMENTS

| | | | |
|---|---|---|---|
| 2006/0024365 A1* | 2/2006 | Vaya | A61K 9/2077 424/468 |
| 2006/0110331 A1 | 5/2006 | Dang | |
| 2008/0200452 A1 | 8/2008 | Obermeier et al. | |
| 2010/0063110 A1* | 3/2010 | Meyer | A61K 31/465 514/343 |
| 2017/0189346 A1* | 7/2017 | Myers | A61K 47/36 |

* cited by examiner

LOXAPINE FILM ORAL DOSAGE FORM

CROSS-REFERENCE TO RELATED APPLICATIONS

This application is a Continuation-in-Part of application Ser. No. 15/014,269, filed Feb. 3, 2016, which is incorporated herein by reference in its entirety.

FIELD OF THE DISCLOSURE

This disclosure relates to loxapine dosage forms that provide rapid onset of therapeutic relief from acute agitation associated with schizophrenia or bipolar 1 disorder.

BACKGROUND OF THE DISCLOSURE

Agitation associated with schizophrenia or bipolar mania is not uncommon, and if left untreated can rapidly escalate into physically aggressive behavior that can be potentially dangerous to the agitated individual and others. In a clinical setting agitation associated with schizophrenia and bipolar mania are often effectively managed with behavioral and psychological techniques, with unexpected acute agitation typically being treated with parenterally administered sedatives such as benzodiazepines and/or antipsychotic drugs such as olanzapine and ziprasidone.

On Dec. 21, 2012, the U.S. Food and Drug Administration approved a loxapine product formulated into an inhaled powder for direct administration to the lungs and is indicated for the treatment of acute agitation associated with schizophrenia or bipolar 1 disorder in adults. A statistically significant reduction in agitation occurs at 2 hours, and an improvement is achieved at 10 minutes after administration. The onset of a statistically significant reduction in agitation occurs at 5 minutes. However, to mitigate the risk of bronchospasm, inhaled loxapine powder must be administered only in an enrolled healthcare facility, and only to patients that have been prescreened to ensure they are not susceptible to pulmonary issues.

Loxapine oral capsules have been available for the treatment of schizophrenia since about 1988, with the typical dosage being 30-50 mg twice daily. The loxapine capsules are unsuitable for treating acute agitation associated with schizophrenia or bipolar 1 disorder because onset of therapeutic relief occurs approximately 20-30 minutes after administration. Such delayed onset of relief would significantly increase the risk of injury to a person being treated and those administering treatment.

There are patients that have been successfully treated for schizophrenia or bipolar 1 disorder so that they can be released from clinical supervision. Nevertheless, there remains a possibility that intermittent acute agitation can occur, such as when the patient fails to take prescribed antipsychotic medication or engages in risky behavior such as indulging in intoxicants. It has been found that such patients feel symptoms of impending acute agitation, and that such acute agitation can be averted if the patient is immediately medicated with loxapine upon feeling symptoms.

A fast acting loxapine dosage form that can be used to effectively treat acute agitation associated with schizophrenia or bipolar 1 disorder in non-institutionalized patients while reducing the risk of pulmonary problems is needed. Such dosage form would substantially reduce risks of violence and injury to patients and others by preventing or reducing the duration and severity of an episode of acute agitation.

SUMMARY OF THE DISCLOSURE

Disclosed is a loxapine film oral dosage form that provides rapid onset of relief from acute agitation associated with schizophrenia or bipolar 1 disorder without exposing patients to bronchospasm or other life threatening complications and without requiring prescreening of patients for pulmonary or other issues. The disclosed loxapine oral dosage form has the further advantage that it can be safely administered either in a clinical facility or outside of a clinical facility.

The disclosed loxapine dosage forms are formulated as orally administered films comprising loxapine salt, free base, or prodrug disposed within or on a polymeric film suitable for oral administration. The films can be formulated for rapid disintegration and distribution of micro- or nanoscopic particles of the active agent in the gastrointestinal tract or as mucoadhesive films that facilitate rapid absorption of loxapine via oral mucosal tissue, i.e., buccal or sublingual film dosage forms.

Also disclosed is a process for treating or ameliorating acute agitation associated with schizophrenia or bipolar 1 disorder by administering to such patients in need of treatment a loxapine film oral dosage form as described herein.

These and other features, advantages and objects of the various embodiments will be better understood with reference to the following specification and claims.

DETAILED DESCRIPTION

Figure 1:
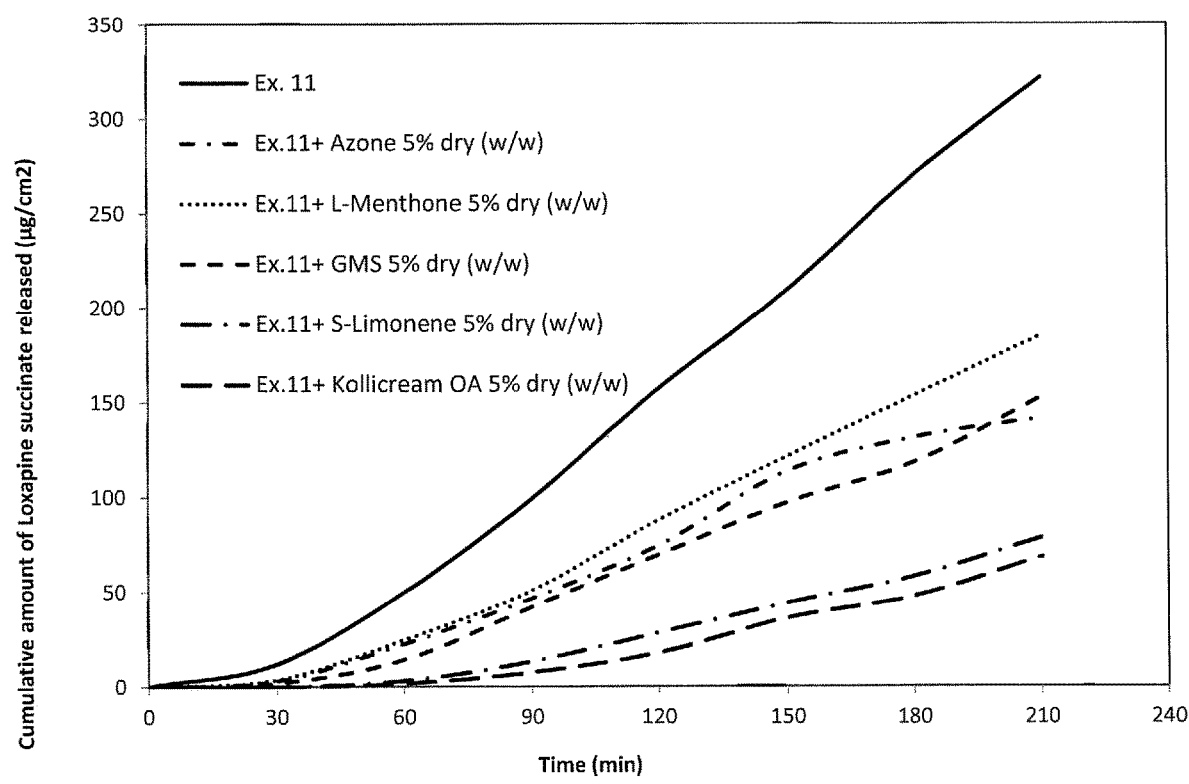
FIG. 1 graphically depicts Loxapine film diffusion through Porcine buccal mucosa (48-hrs-old unfrozen fresh mucosa) (Franz cell 1.76 cm2; 37° C.); saliva pH 6.8.

The films comprising loxapine salt, prodrug, or free base disposed in or on a polymeric film-forming system can beneficially include a refreshing agent, a sweetener, a permeation enhancer, an antioxidant, a pH stabilizer or pH stabilizing system, or a combination of two or more of the foregoing components.

Loxapine has the IUPAC name 2-chloro-11-(4-methylpiperazin-1-yl) dibenzo [b,f] [1,4] oxazepine. It is predominantly used as an antipsychotic medication for the treatment of schizophrenia and bipolar 1 disorder. Such medications are currently sold under the tradenames "Loxapac" and "Loxitane." An inhalable form, sold under the tradename "Adasuve" is indicated for the rapid treatment of acute agitation associated with schizophrenia or bipolar 1 disorder, but is limited to clinical use in approved facilities on prescreened patients that are not susceptible to pulmonary problems.

Pharmaceutically acceptable salts that may be used in the film dosage forms disclosed herein include generally any salt that has been or may be approved by the US FDA or other appropriate foreign or domestic agency for administration to a human. Non-limiting examples include hydrochloric, hydrobromic, nitric, carbonic, monohydrocarbonic, phosphoric, monohydrogen phosphoric, dihydrogen phosphoric acid, sulfuric acid, a hydrogen sulfuric acid, and hydroiodic acids of loxapine. Other examples include salts derived from nontoxic organic acids, including acetic, propionic, isobutyric, maleic, malonic, benzoic, succinic, suberic, fumaric, lactic, mandelic, phthalic, benzenesulfonic, p-toluenesulfonic, citric, tartaric, and methanesulfonic acids, or combinations of these acid salts.

Pharmaceutically acceptable prodrugs that may be used in the film dosage forms disclosed herein include any pharmaceutically acceptable compounds that react in vivo to produce loxapine. Examples of loxapine prodrugs include the phosphonooxymethyl prodrugs of loxapine described in Krise et al., J. Pharm. Sci. (1999) 88:922.

The active loxapine agent can comprise about 2% to 25% or 5% to 20% of the weight of the film on a dry basis.

The polymeric film forming system can comprise a single pharmaceutically acceptable film-forming polymer or a combination of film-forming polymers. Examples of film-forming polymers that can be used for preparing the disclosed loxapine dosage forms include polyethylene oxide, povidone (polyvinylpyrrolidone), copovidone (copolymers of N-vinyl-2-pyrrolidone and vinyl acetate), polyvinyl alcohol, polyethylene glycol, polyacrylic acid, methylmethacrylate copolymer, carboxyvinyl copolymers, polydextrose, pullulan, hydroxypropylmethyl cellulose, hydroxyethyl cellulose, hydroxypropyl cellulose, carboxymethyl cellulose, sodium alginate, xanthan gum, tragancath gum, guar gum, acacia gum, arabic gum, starch and gelatin.

The selection of film-forming polymers can be made to dissolve completely over a period of time that is sufficient to ensure delivery of a therapeutically effective amount of loxapine via oral mucosa, yet not so long as to cause annoyance or discomfort to the subject being administered loxapine. For example, a film dosage form can be formulated to reside in the buccal cavity or sublingual region for a period of from 1 minute to an hour, 4 minutes to 50 minutes, 5 minutes to 45 minutes, 10 minutes to 30 minutes, or 15 minutes to 30 minutes. There is a high variation from 1 minute to an hour from subject to subject. The film-forming polymer or combination of film-forming polymers can comprise 10% to 90%, 20% to 80% or 30% to 70% of the weight of the film oral dosage form on a dry basis. Povidone (polyvinylpyrrolidone) can be present in an amount of from 3% to 50% by weight of the film on a dry basis.

Because of the taste of loxapine, which is generally perceived as unpleasant, it is beneficial to add a sweetener, flavoring agent, refreshing agent, taste-masking agent, or a combination of these materials. Examples of sweeteners that can be used in the disclosed loxapine film dosage forms include acesulfame potassium, aspartame, aspartan-acesulfame salt, cyclamate, erythritol, glycerol, glycyrrhizin, hydrogenated starch hydrolysate, isomalt, lactitol, maltitol, mannitol, neotame, polydextrose, saccharin, sorbitol, sucralose, tagatose, xylitol, dextrose, glucose, fructose, and honey. Flavoring agents that can be added to the disclosed loxapine film dosage forms include isoamyl acetate (banana flavor), benzaldehyde (cherry flavor), cinnamaldehyde (cinnamon flavor), ethyl propionate (fruit flavor), methyl anthranilate (grape flavor), limonene (orange flavor), ethyl decadienoate (pear flavor), allyl hexanoate (pineapple flavor), ethyl meltol, ethylanillin (vanilla flavor), and methyl salicylate (wintergreen flavor). Refreshing agents, also called cooling agents, are chemicals that trigger the cold sensitive receptors creating a cold sensation. Refreshing agents that can be added to the loxapine film oral dosage forms disclosed herein include menthol, thymol, camphor and eucalyptol.

Sweeteners, flavoring agents, and refreshing agents can be added in conventional quantities, generally up to a total amount of 5% to 10% of the weight of the film on a dry basis, e.g., 0.1% to 10%, or 0.5% to 5%.

The loxapine film oral dosage forms disclosed herein can advantageously employ an antioxidant or oxygen scavenger to prevent or reduce oxidative degradation of the loxapine salt, free base or prodrug prior to use. Examples of oxygen scavengers or antioxidants that substantially improve long-term stability of a loxapine film oral dosage form against oxidative degradation of the active agent are sulfite salts such as sodium sulfite, sodium bisulfite, sodium metabisulfite and analogous salts of potassium and calcium.

A suitable amount of salt (e.g., sodium sulfite) is from about 0.01% to 5% or 0.1% to 1% of the weight of the film on a dry basis.

It was discovered that absorption of loxapine through oral mucosa is significantly enhanced when the film formulation is maintained at a neutral pH of from 6 to 8, or 6.5 to 7.5. Because the blend of film forming polymers and other ingredients tend to create an acidic pH, it is beneficial to add an alkaline substance that increases the pH of the film product and stabilizes the film at a neutral pH. Examples of pH stabilizers that can be added to the films disclosed herein include bicarbonates (e.g., sodium bicarbonate), citrates (e.g., potassium citrate), carbonates (e.g., calcium carbonate), lactates (e.g., sodium lactate), and acetates (e.g., calcium acetate). The final pH of the film product is evaluated by placing two pieces of film cut to the target size for drug loading (1-6 cm$^2$), in 10 mL of Milli-Q purified water. The films are mixed using a stir until completely solubilized and then the pH of the resulting solution is measured and recorded.

Sodium bicarbonate or other pH stabilizers can be added to the loxapine film oral dosage forms disclosed herein in amounts effective to stabilize the pH within a range of from 6 to 8 or 6.5 to 7.5, with a suitable amount being, for example, 0.5% to 10% or 1% to 5% based on the weight of the film on a dry basis.

To further promote absorption of loxapine salt, free-base or prodrug through oral mucosa and reduce the amount of loxapine that is introduced into the gastrointestinal tract, it is advantageous to add to the loxapine film formulation a penetration enhancer. It has been discovered that a particularly effective penetration enhancer that promotes absorption of loxapine via oral mucosa is hyaluronic acid or salts thereof. According to some embodiment, a penetration enhancer, such as hyaluronic acid or bile salt, is added to the loxapine film oral dosage form in an amount of from about 0.1% to about 10%, 0.5% to 5%, or 1% to 3% of the weight of the film dosage form on a dry basis to significantly enhance absorption of loxapine from the film through oral mucosa.

According to embodiments, to promote adhesion of the loxapine film oral dosage form to oral mucosa, it is advantageous to add a mucoadhesive agent to the oral film product. Examples of mucoadhesive agents that can be added to the loxapine film oral dosage form to promote adhesion to oral mucosa include sodium alginate, sodium carboxymethyl cellulose, guar gum, hydroxyethyl cellulose, hydroxypropyl cellulose, hydroxypropylmethyl cellulose, karya gum, methylcellulose, polyethylene oxide, retene and tragacanth. Such mucoadhesive agent may be added to the film formulation in an amount of from about 0.5% to about 20%, or about 1% to about 5%, of the total weight of the film on a dry basis.

Plasticizers can be advantageously employed in the film formulations as needed to suitably modify the flexibility of the film to facilitate processing and allow the film to easily conform to the shape of the oral mucosa to which the film is applied. Plasticizers that can be effectively employed in the disclosed loxapine film oral dosage forms to improve flexibility of the film include ethylene glycol, propylene glycol, tributyl citrate, triethyl citrate and glycerol. Depending on the selected film-forming polymers and other components of the film formulation, a suitable amount of plasticizer is typically from about 0.1% to 10%, 0.5% to 5%, or 1% to 5%.

Bulking agents or fillers may be added as desired to increase the size of the finished film product to facilitate processing and manufacturing, or to modify properties (e.g., increase or decrease residence time or increase stiffness) of the film formulation. Suitable fillers that can be added to the disclosed film products include starch, calcium salts, such as calcium carbonate, and sugars, such as lactose. The amount of fillers that can be added to the film oral dosage forms disclosed herein are typically up to about 25%, 0.5% to 20%, 1% to 15% or about 2% to about 10% of the weight of the film on a dry basis.

The loxapine film oral dosage forms disclosed herein can be prepared by dissolving or finely dispersing the loxapine salt, free base or prodrug and film forming polymers in a solvent, along with any other desired additives, including, but not limited to a pH stabilizer, an antioxidant, a plasticizer, a penetration enhancer, a mucoadhesive agent, a flavoring agent, a coloring agent, a freshening agent, a sweetener, a filler, or a combination of additives. The films may then be cast on a suitable substrate by removing (e.g., evaporating) the solvent or solvents from the formulation to produce a dry film. Typically, the loxapine film can be cast to produce a film having a thickness of from 100 micrometers to 1.5 millimeters or 500 micrometers to 1000 micrometers. The dry film can be cut in appropriate sizes, typically an area of from about 1 square centimeter to about 15 square centimeters, to provide an appropriate dose for transmucosal delivery of loxapine salt, free base, or prodrug, to treat acute agitation associated with schizophrenia or bipolar 1 disorder.

In accordance with a particular aspect of this disclosure it is beneficial to provide a film dosage form that concurrently maintains a neutral pH while keeping the loxapine fully or nearly completely dissolved. Unfortunately, the solubility of loxapine is especially low at or near neutral pH. However, it has been discovered that by employing methanol and/or ethanol as a solvent or cosolvent during preparation of a loxapine film, and using povidone (polyvinylpyrrolidone) as a film-forming polymer in the formulation in an amount of from 5% to 50% or 10% to 40% by weight of the film on a dry basis, it is possible to concurrently add a pH stabilizer to maintain neutral pH while maintaining the loxapine in a highly dissolved form, thereby promoting rapid transmucosal absorption and rapid onset of a desirable therapeutic effect. It is believed that the addition of polyethylene glycol (plasticizer) and sodium hyaluronate (penetration enhancer) also significantly contribute to rapid absorption and onset of a desired therapeutic effect.

Figure 2:
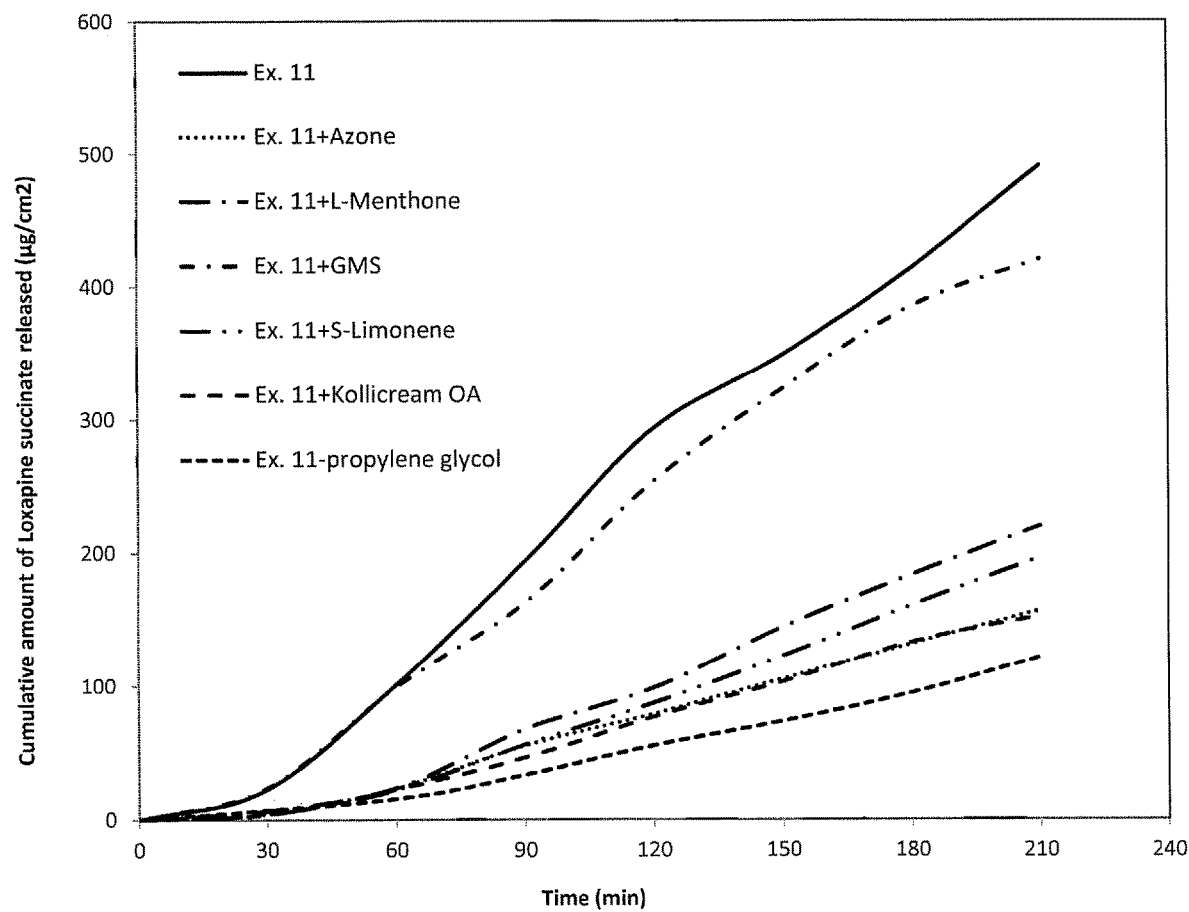
FIG. 2 graphically depicts Loxapine film diffusion through Porcine buccal mucosa (26-hrs-old unfrozen fresh mucosa) (Franz cell 1.76 cm2; 37° C.); saliva pH 6.8.
Figure 3:
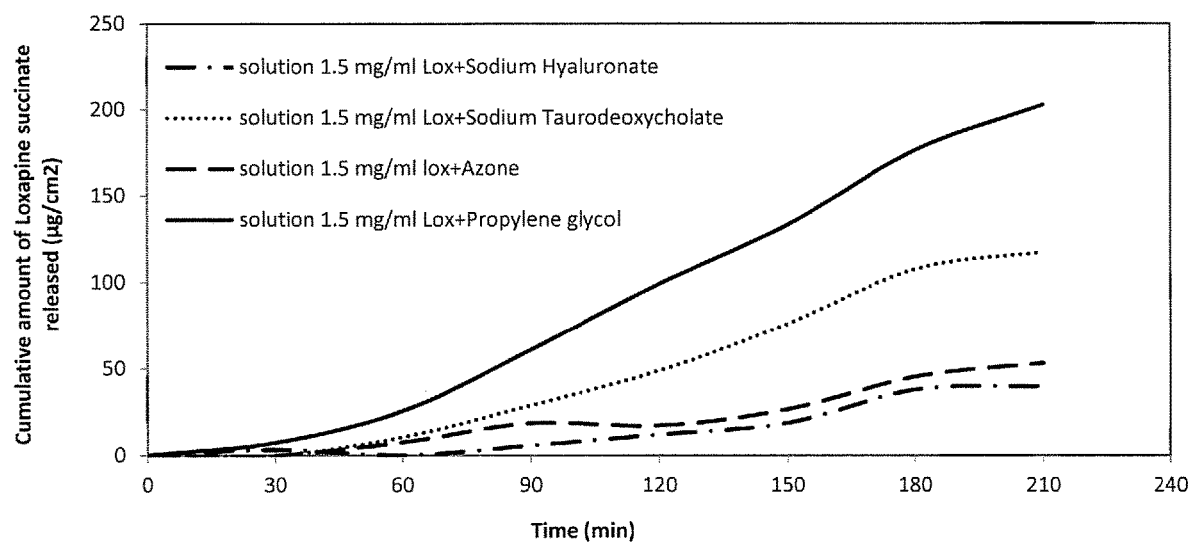
FIG. 3 graphically depicts Loxapine Solutions-diffusion through Porcine buccal mucosa (fresh mucosa kept at 4 C for 48 hours) (Franz cell 1.76 cm2; 37° C.); saliva pH 6.8.

It was found that the permeation and absorption of loxapine in the oral cavity is greatly enhanced through the use of a single or combination of penetration enhancers present in the formulation in the range of 0.05-8.00% dry w/w. These penetration enhancers include sulphoxides (dimethylsulphoxide, decylmethyl sulfoxide), azones (laurocapram), pyrrolidones (2pyrrolidone, 2P), alcohols/alkanols (ethanol or decanol), glycols (propylene glycol), surfactants (anionic, sodium lauryl sulfate, sodium decyl sulfate), (Nonionic, Tween, PLE), (Cationic, chitosan, cetylpyridinium chloride), terpenes (1,8-cineole, menthol, and menthone, D-limonene), fatty acids (oleic acid, sodium caprate), and bile salts (sodium deoxycholate, sodium deoxyglycocholate). From the data we acquired propylene glycol appeared to have a significantly discernable effect on permeation of loxapine delivered through oral films (see FIGS. 1-3). It was surprisingly found that not all permeation enhancers were able to improve loxapine absorption/permeation through the mucosa. Some permeation enhancers such as Eucalyptol and SLS were even found to reduce absorption/permeation of the loxapine. Other permeation enhancers (see TABLE 17) had no effect on the absorption/permeation of loxapine in oral films.

In certain embodiments the oral film may be designed as bilayer or multilayer product. The bilayer the oral film consists of at least one an active layer containing the drug and at least one backing layer. The active layer is designed to be placed on and adhere to the oral mucosa with the backing layer oriented outwards away from the mucosa. According to these embodiments, the backing layer is used to protect the active layer from abrasion occurring from mastication and tongue movement. The backing layer thus promote or direct absorption of the drug from the active layer into the underlying vascular network.

According to embodiments, multilayer oral film designs are used to combine multiple active drugs into a single dosage. Accordingly, the disclosed oral film would consist of 2 or more distinct active layers in combination with at least one protective backing layer. In other embodiments the backing layer may contain neutralization agents to mitigate skin irritation or promote a pleasant taste or mouth feel to improve patient compliance. The ratio of active layer(s) to backing layer can be modified as needed to determine film thickness, weight and residence time in the mouth.

The following Examples are illustrative of the present invention:

TABLE 1

Formulation for Example Film 1

| Ingredients | % wet (w/w) | % dry (w/w) | Function |
| --- | --- | --- | --- |
| Water | 22.7 | — | Solvent |
| Methanol | 53.1 | — | Solvent |
| Sodium Bicarbonate | 0.5 | 2.2 | pH Stabilizer |
| Sodium sulfite | 0.1 | 0.4 | Antioxidant |
| Polyethylene Glycol | 1.2 | 5.0 | Plasticizer |
| Sodium taurodeoxycholate | 0.6 | 2.6 | Penetration Enhancer |
| Polyethylene Oxide | 1.5 | 6.1 | Mucoadhesive |
| Loxapine succinate | 2.1 | 8.8 | Active |
| L-Menthol | 0.1 | 0.6 | Freshening Agent And Taste Masking Agent |
| Sucralose | 0.2 | 0.8 | Sweetener |
| Calcium Carbonate | 1.7 | 7.0 | Filler |
| Povidone | 4.9 | 20.4 | Film-Former |
| Hydroxypropyl cellulose | 11.2 | 46.1 | Film-Former |
| Total | 100.0 | 100.0 | |

TABLE 2

Formulation for Example Film 2

| Ingredients | % wet (w/w) | % dry (w/w) | Function |
|---|---|---|---|
| Water | 22.7 | — | Solvent |
| Methanol | 53.0 | — | Solvent |
| Sodium Bicarbonate | 0.5 | 2.2 | pH Stabilizer |
| Sodium sulfite | 0.1 | 0.4 | Antioxidant |
| Polyethylene Glycol | 1.2 | 5.0 | Plasticizer |
| Sodium Hyaluronate | 0.6 | 2.5 | Penetration Enhancer |
| Polyethylene Oxide | 1.5 | 6.1 | Mucoadhesive |
| Loxapine succinate | 3.3 | 13.7 | Active |
| L-Menthol | 0.1 | 0.6 | Freshening Agent And Taste Masking Agent |
| Sucralose | 0.2 | 0.8 | Sweetener |
| Calcium Carbonate | 1.7 | 7.0 | Filler |
| Povidone | 4.9 | 20.3 | Film-Former |
| Hydroxypropyl cellulose | 10.1 | 41.4 | Film-Former |
| Total | 100.0 | 100.0 | |

TABLE 3

Formulation for Example Film 3

| Ingredients | % wet (w/w) | % dry (w/w) | Function |
|---|---|---|---|
| Water | 23.0 | — | Solvent |
| Methanol | 53.8 | — | Solvent |
| Sodium Bicarbonate | 0.6 | 2.6 | pH Stabilizer |
| Butylated Hydroxytoluene | 0.01 | 0.02 | Antioxidant |
| Polyethylene Glycol | 1.3 | 5.5 | Plasticizer |
| Polyethylene Oxide | 1.8 | 7.6 | Mucoadhesive |
| Sodium metabisulfite | 0.01 | 0.2 | Antioxidant |
| Loxapine succinate | 3.7 | 15.7 | Active |
| L-Menthol | 0.4 | 1.6 | Permeation Enhancer And Refreshing Agent |
| Sucralose | 0.2 | 0.9 | Sweetener |
| FD&C Blue No 2 | 0.02 | 0.1 | Colorant |
| Povidone | 5.0 | 21.7 | Film-Former |
| Hydroxypropyl cellulose | 10.2 | 44.1 | Film-Former |
| Total | 100.00 | 100.00 | |

TABLE 4

Formulation for Example Film 4

| Ingredients | % wet (w/w) | % dry (w/w) | Function |
|---|---|---|---|
| Methanol | 74.1 | — | Solvent |
| Sodium Bicarbonate | 0.6 | 2.2 | pH Stabilizer |
| Sodium bisulfite | 0.1 | 0.2 | Antioxidant |
| Triacetin | 3.3 | 12.7 | Plasticizer |
| Copovidone | 1.7 | 6.7 | Film-Former |
| Loxapine succinate | 3.0 | 11.6 | Active |
| L-Menthol | 0.3 | 1.1 | Permeation Enhancer And Refreshing Agent |
| Sucralose | 0.3 | 1.1 | Sweetener |
| Povidone | 5.4 | 21.1 | Film-Former |
| Hydroxypropyl cellulose | 11.2 | 43.3 | Film-Former |
| Total | 100.0 | 100.0 | |

TABLE 5

Formulation for Example Film 5

| Ingredients | % wet (w/w) | % dry (w/w) | Function |
|---|---|---|---|
| Ethanol | 71.8 | — | Solvent |
| Water | 8.0 | — | Solvent |
| Sodium Bicarbonate | 0.5 | 2.6 | pH Stabilizer |
| Sodium metabisulfite | 0.04 | 0.2 | Antioxidant |
| Glycerin | 0.8 | 3.9 | Plasticizer |
| Copovidone | 1.6 | 7.9 | Film-Former |
| Loxapine succinate | 2.9 | 14.5 | Active |
| Sucralose | 0.3 | 1.3 | Sweetener |
| L-Menthol | 0.2 | 1.1 | Permeation Enhancer And Refreshing Agent |
| Povidone | 5.9 | 29.1 | Film-Former |
| Hydroxypropyl cellulose | 8.0 | 39.4 | Film-Former |
| Total | 100.0 | 100.0 | |

TABLE 6

Formulation for Example Film 6

| Ingredients | % wet (w/w) | % dry (w/w) | Function |
|---|---|---|---|
| Water | 22.7 | — | Solvent |
| Methanol | 53.0 | — | Solvent |
| Sodium Bicarbonate | 0.6 | 2.2 | pH Stabilizer |
| Sodium metabisulfite | 0.1 | 0.4 | Antioxidant |
| Polyethylene Glycol | 1.2 | 5.0 | Plasticizer |
| Sodium glycodeoxycholate | 0.6 | 2.5 | Penetration Enhancer |
| Polyethylene Oxide | 1.5 | 6.1 | Mucoadhesive |
| Loxapine succinate | 3.3 | 13.7 | Active |
| L-Menthol | 0.1 | 0.6 | Freshening Agent And Taste Masking Agent |
| Sucralose | 0.2 | 0.8 | Sweetener |
| Calcium Carbonate | 1.7 | 7.0 | Filler |
| Povidone | 10.1 | 41.4 | Film-Former |
| Hydroxypropyl cellulose | 4.9 | 20.3 | Film-Former |
| Total | 100.0 | 100.0 | |

TABLE 7

Formulation for Example Film 7

| Ingredients | % wet (w/w) | % dry (w/w) | Function |
|---|---|---|---|
| Water | 64.5 | — | Solvent |
| Ethanol | 10.0 | — | Solvent |
| Sodium taurodeoxycholate | 0.7 | 2.6 | Penetration Enhancer |
| Polyethylene Glycol | 1.3 | 5.2 | Plasticizer |
| Sodium bicarbonate | 0.7 | 2.6 | pH Stabilizer |
| Hypromellose | 5.0 | 19.4 | Film-Former |
| Hypromellose | 1.3 | 5.3 | Film-Former |
| Polyethylene Oxide | 10.8 | 42.3 | Film-Former |
| Loxapine succinate | 5.3 | 21.0 | Active |
| Evospray Lime Flavor | 0.4 | 1.6 | Flavoring Agent |
| Total | 100.0 | 100.0 | |

TABLE 8

Formulation for Example Film 8

| Ingredients | % wet (w/w) | % dry (w/w) | Function |
|---|---|---|---|
| Ethanol | 71.6 | — | Solvent |
| Water | 8.0 | — | Solvent |
| Sodium Bicarbonate | 0.5 | 2.6 | pH Stabilizer |
| Sodium metabisulfite | 0.04 | 0.2 | Antioxidant |
| Glycerin | 0.6 | 3.9 | Plasticizer |
| Copovidone | 1.8 | 7.9 | Film-Former |
| Loxapine succinate | 3.9 | 14.5 | Active |
| Sucralose | 0.3 | 1.3 | Sweetener |
| D-limonene | 0.4 | 1.1 | Permeation Enhancer |
| Povidone | 4.9 | 29.1 | Film-Former |
| Hydroxypropyl cellulose | 8.0 | 39.4 | Film-Former |
| Total | 100.0 | 100.0 | |

TABLE 9

Formulation for Example Film 9

| Ingredients | % wet (w/w) | % dry (w/w) | Function |
|---|---|---|---|
| Water | 22.7 | — | Solvent |
| Methanol | 53.1 | — | Solvent |
| Sodium Bicarbonate | 0.1 | 2.2 | pH Stabilizer |
| Sodium sulfite | 0.1 | 0.4 | Antioxidant |
| Polyethylene Glycol | 1.2 | 5.0 | Plasticizer |
| Sodium taurodeoxycholate | 0.3 | 2.6 | Penetration Enhancer |
| Polyethylene Oxide | 1.5 | 6.1 | Mucoadhesive |
| Loxapine succinate | 2.1 | 8.8 | Active |
| Laurocapram | 0.1 | 0.6 | Penetration Enhancer |
| Sucralose | 0.2 | 0.8 | Sweetener |
| Calcium Carbonate | 1.7 | 7.0 | Filler |
| Povidone | 4.1 | 20.4 | Film-Former |
| Hydroxypropyl cellulose | 11.2 | 46.1 | Film-Former |
| Total | 100.0 | 100.0 | |

TABLE 10

Formulation for Example Film 10

| Ingredients | % wet (w/w) | % dry (w/w) | Function |
|---|---|---|---|
| *Active Layer Composition* | | | |
| Methanol | 74.1 | — | Solvent |
| Sodium Bicarbonate | 0.6 | 2.2 | pH Stabilizer |
| Sodium bisulfite | 0.1 | 0.2 | Antioxidant |
| Triacetin | 3.3 | 12.7 | Plasticizer |
| Copovidone | 1.7 | 6.7 | Film-Former |
| Loxapine succinate | 3.0 | 11.6 | Active |
| L-Menthol | 0.3 | 1.1 | Permeation Enhancer And Refreshing Agent |
| Sucralose | 0.3 | 1.1 | Sweetener |
| Povidone | 5.4 | 21.1 | Film-Former |
| Hydroxypropyl cellulose | 11.2 | 43.3 | Film-Former |
| Total | 100.0 | 100.0 | |
| *Backing Layer Composition* | | | |
| Methanol | 77.8 | — | Solvent |
| Triacetin | 3.3 | 14.8 | Plasticizer |
| Copovidone | 1.7 | 7.8 | Film-Former |
| L-Menthol | 0.3 | 1.3 | Permeation Enhancer And Refreshing Agent |
| Sucralose | 0.3 | 1.3 | Sweetener |
| Povidone | 5.4 | 24.5 | Film-Former |
| Hydroxypropyl cellulose | 11.2 | 50.3 | Film-Former |
| Total | 100.0 | 100.0 | |

TABLE 11

Formulation for Example Film 11

| Ingredients | % wet (w/w) | % dry (w/w) | Function |
|---|---|---|---|
| Methanol | 71.3 | — | Solvent |
| Propylene Glycol | 2.6 | 9.0 | Penetration Enhancer |
| Menthol | 0.4 | 1.5 | Refreshing Agent |
| Sucralose | 0.2 | 0.7 | Sweetener |
| Sodium sulfite | 0.1 | 0.4 | Antioxidant |
| sodium bicarbonate | 0.3 | 1.1 | pH Stabilizer |
| D&C yellow#10 Lake | 0.04 | 0.1 | Colorant |
| Loxapine succinate | 4.6 | 16.0 | Active |
| Titanium dioxide | 0.7 | 2.6 | Opacifier |
| Povidone | 6.8 | 23.7 | Film-Former |
| Hydroxypropyl cellulose | 12.9 | 44.9 | Film-Former |
| Total | 100.0 | 100.0 | |

TABLE 12

Formulation for Example Film 12

| Ingredients | % wet (w/w) | % dry (w/w) | Function |
|---|---|---|---|
| Methanol | 37.9 | — | Solvent |
| Purified water | 37.9 | — | Solvent |
| Propylene Glycol | 2.3 | 9.5 | Plasticizer |
| L-Menthol | 0.4 | 1.5 | Refreshing Agent |
| Sucralose | 0.2 | 0.8 | Sweetener |
| Sodium sulfite | 0.1 | 0.4 | Antioxidant |
| Loxapine succinate | 3.9 | 16.0 | Active |
| Sodium bicarbonate | 0.5 | 2.2 | pH Stabilizer |
| D&C yellow#10 Lake | 0.04 | 0.1 | Colorant |
| Hypromellose | 4.4 | 18.2 | Film-Former |
| Hydroxypropyl cellulose | 12.4 | 51.2 | Film-Former |
| Total | 100.0 | 100.0 | |

TABLE 13

Formulation for Example Film 13

| Ingredients | % wet (w/w) | % dry (w/w) | Function |
|---|---|---|---|
| Methanol | 53.1 | — | Solvent |
| Purified water | 22.8 | — | Solvent |
| Sodium Bicarbonate | 0.5 | 2.2 | pH Stabilizer |
| Sodium Sulfite | 0.1 | 0.4 | Antioxidant |
| Polyethylene Glycol | 1.2 | 5.0 | Plasticizer |
| Sodium Hyaluronate | 0.6 | 2.6 | Penetration Enhancer |
| Polyethylene Oxide | 1.5 | 6.2 | Mucoadhesive |
| Loxapine succinate | 3.3 | 13.6 | Active |
| L-Menthol | 0.1 | 0.6 | Refreshing Agent |
| Sucralose | 0.2 | 0.8 | Sweetener |

TABLE 13-continued

Formulation for Example Film 13

| Ingredients | % wet (w/w) | % dry (w/w) | Function |
|---|---|---|---|
| Calcium Carbonate | 1.7 | 7.1 | Filler |
| Povidone | 4.9 | 20.4 | Film-Former |
| Hydroxypropyl cellulose | 10.0 | 41.2 | Film-Former |
| Total | 100.0 | 100.0 | |

TABLE 14

Formulation for Example Film 14

| Ingredients | % wet (w/w) | % dry (w/w) | Function |
|---|---|---|---|
| Methanol | 53.8 | — | Solvent |
| Purified water | 23.0 | — | Solvent |
| Loxapine succinate | 3.6 | 15.7 | Active |
| Sodium Bicarbonate | 0.6 | 2.6 | pH Stabilizer |
| FD&C blue No2 | 0.0 | 0.1 | Colorant |
| Polyethylene Oxide | 1.8 | 7.7 | Mucoadhesive |
| BHT | 0.005 | 0.02 | Antioxidant |
| Polyethylene Glycol | 1.3 | 5.5 | Plasticizer |
| L-Menthol | 0.4 | 1.5 | Refreshing Agent |
| Sucralose | 0.2 | 0.9 | Sweetener |
| Povidone | 5.0 | 21.7 | Film-Former |
| Hydroxypropyl cellulose | 10.2 | 44.2 | Film-Former |
| Total | 100.0 | 100.0 | |

TABLE 15 pH measurements for Example Films 11-14

| Loxapine Film formulation | Surface method* Measured pH | solution method** Measured pH | Deionised water pH |
|---|---|---|---|
| Ex. 11 | 6.03 | 5.36 | 5.6 |
| Ex. 12 | 5.92 | 5.82 | 5.6 |
| Ex. 13 | 6.42 | 7.22 | 5.6 |
| Ex. 14 | 5.95 | 5.92 | 5.6 |

*Put a drop of D.I. water on a small area of the film, bring the pH probe in contact with the wet area for few second and measure the pH
**Dissolve or disperse completely 2 pieces of films in 10 ml D.I. put the pH probe into the solution and measure the pH

TABLE 16

Film Characteristics for Example Films 11-14

| Loxapine Film formulation | Formulation characteristics | Age of tested films (stored in pouches at room T) | Loxapine precipitation |
|---|---|---|---|
| Ex. 11 | Methanol based formulation | 12 months | opaque |
| Ex. 12 | 50% water/50% methanol based formulation | 12 months | No precipitation |
| Ex. 13 | 30% water/70% methanol based formulation, it contains dispersed calcium carbonate | 16 months | No precipitation |
| Ex. 14 | 30% water/70% methanol based formulation | 16 months | signs of precipitation on the film |

TABLE 17

Penetration enhancer and their effect on Loxapine absorption

| Chemical Penetration Enhancer | Effect on loxapine absorption/ permeation | physical state of permeation enhancer |
|---|---|---|
| Sodium deoxycholate | positif effect (+) | Solid |
| Sodium Glycodeoxycholate | positif effect (++) | Solid |
| Sodium Taurocholate | positif effect (+) | Solid |
| Sodium Taurodeoxycholate | positif effect (+) | Solid |
| Hyaluronate sodium | positif effect (++) | Solid |
| Propylene Glycol | positif effect (++) | Liquid |
| D-α-Tocopherol Vitamin E 1000 succinate (TPGS) | positif effect (+) | Solid |
| Phosphatidylcholine (Lecithin, soybean) | positif effect (+) | Solid |
| Benzalkonium chloride | no effect | Solid |
| Cetylpyridinium chloride | no effect | Solid |
| polysorbate 80 (Tween 80) (Polyethylene glycol sorbitan monooleate) | no effect | Liquid |
| Ethylenediaminetetraacetic acid calcium disodium (EDTA salt) | no effect | Solid |
| Sodium lauryl sulphate (SLS) | negative effect (−) | Liquid |
| Eucalyptol | negative effect (−) | Liquid |
| L-menthone | positif effect (+) | Liquid |
| Glyceryl monostearate (GMS) | positif effect (++) | Solid |
| (S)-(−)-Limonene | positif effect (+) | Liquid |
| Azone (laurocapram) | positif effect (+) | Liquid |
| Oleyl alcohol (Kollicream OA) | positif effect (+) | Solid |

The above description is considered that of the preferred embodiment(s) only. Modifications of these embodiments will occur to those skilled in the art and to those who make or use the illustrated embodiments. Therefore, it is understood that the embodiment(s) described above are merely exemplary and not intended to limit the scope of this disclosure, which is defined by the following claims as interpreted according to the principles of patent law, including the doctrine of equivalents.

The invention claimed is:

1. A loxapine film oral dosage form, comprising:
loxapine salt, free base, or prodrug in an amount that is effective to provide relief from acute agitation associated with schizophrenia or bipolar 1 disorder via transmucosal delivery route;
the loxapine salt, free base, or prodrug dispersed in a polymeric film including a combination of film forming polymers selected to cause the film oral dosage form to reside and dissolve in the buccal cavity or sublingual region of a subject being administered the loxapine film oral dosage form for a period of from 4 minutes to 50 minutes, and wherein the oral film dosage form includes an alkaline substance that increases the pH of the oral film dosage form to maintain a neutral pH of from 6 to 8, the selected combination of film forming polymers comprising from 39.4% to 51.2% hydroxypropyl cellulose or polyethylene oxide by weight of the film oral dosage form on a dry basis and from 18.2% to 29.1% polyvinylpyrrolidone or hydroxypropyl methyl cellulose by weight of the film oral dosage form on a dry basis.

2. The loxapine film oral dosage form of claim 1, wherein the film forming system formulated to reside in the buccal cavity or sublingual region of a subject being administered the loxapine film oral dosage form for a period of from 5 minutes to 45 minutes.

3. The loxapine film oral dosage form of claim 1, wherein the film forming system formulated to reside in the buccal cavity or sublingual region of a subject being administered the loxapine film oral dosage form for a period of from 10 minutes to 30 minutes.

4. The loxapine film oral dosage form of claim 1, further comprising an antioxidant.

5. The loxapine film oral dosage form of claim 1, further comprising a pH stabilizer.

6. The loxapine film oral dosage form of claim 1, further comprising a penetration enhancer.

7. The loxapine film oral dosage form of claim 1, further comprising a mucoadhesive agent.

8. The loxapine film oral dosage form of claim 1, further comprising a plasticizer.

9. The loxapine film oral dosage form of claim 1, in which the polymeric film-forming system comprises povidone in an amount of from 3% to 50% by weight of the film on a dry basis.

10. The loxapine film oral dosage form of claim 9, further comprising sulfite salts in an amount effective to promote the stability of the film.

11. The loxapine film oral dosage form of claim 10, further comprising polyethylene glycol in an amount effective to increase the flexibility of the film.

12. The loxapine film oral dosage form of claim 11, further comprising sodium hyaluronate or sodium taurodeoxycholate and/or sodium glycodeoxycholate in an amount effective to promote enhanced absorption of loxapine via mucosal tissue.

* * * * *